(12) United States Patent
Pauly

(10) Patent No.: US 6,216,707 B1
(45) Date of Patent: Apr. 17, 2001

(54) **USE OF AT LEAST AN *IRVINGIA GABONENSIS* EXTRACT IN A COSMETIC AND/OR PHARMACEUTICAL PRODUCT**

(75) Inventor: Gilles Pauly, Nancy (FR)

(73) Assignee: Laboratoires Serobiologiques Societe Anonyme, Pulnoy (FR)

(*) Notice: Subject to any disclaimer, the term of this patent is extended or adjusted under 35 U.S.C. 154(b) by 0 days.

(21) Appl. No.: 09/402,834

(22) PCT Filed: Mar. 17, 1998

(86) PCT No.: PCT/FR98/00538

§ 371 Date: Oct. 13, 1999

§ 102(e) Date: Oct. 13, 1999

(87) PCT Pub. No.: WO98/46204

PCT Pub. Date: Oct. 22, 1998

(30) Foreign Application Priority Data

Apr. 14, 1997 (FR) .................................................. 97/04732

(51) Int. Cl.[7] ................................ A61K 7/06; A61K 7/08
(52) U.S. Cl. ........................... 132/202; 132/203; 132/200; 424/70.12
(58) Field of Search ..................................... 132/202, 203, 132/200, 205, 206; 427/70.13, 70.11, 70.05, 70.1; 514/880

(56) References Cited

U.S. PATENT DOCUMENTS

| 3,964,500 | | 6/1976 | Drakoff . | |
|---|---|---|---|---|
| 6,045,779 | * | 4/2000 | Mueller et al. | 132/202 |
| 6,071,504 | * | 6/2000 | Kawai et al. | 132/208 |
| 6,076,530 | * | 6/2000 | Braida-valerio et al. | 132/206 |

OTHER PUBLICATIONS

Eugene N. Onyeike et al., "Effect of Heat–Treatment and Defatting on the Proximate Composition of Some Nigerian Local Soup Thickeners", Food Chemistry, vol. 53, No. 2, 1995, GB, pp. 173–175.

J. O. Onyechi et al., "The Tabletting Properties of Dika Fat Lubricant", Drud. Dev. Ind. Pharm., vol. 16, No. 7, 1990, pp. 1203–1216.

* cited by examiner

*Primary Examiner*—Pedro Philogene
(74) *Attorney, Agent, or Firm*—Young & Thompson

(57) ABSTRACT

The use of at least an *Irvingia gabonensis* extract, in particular *Irvingia gabonensis* seeds, as active agent(s) for preparing a cosmetic and/or pharmaceutical product for topical use on the skin and/or superficial body growth, the extract being present between 0.05% and 50.00% by weight.

18 Claims, No Drawings

USE OF AT LEAST AN *IRVINGIA GABONENSIS* EXTRACT IN A COSMETIC AND/OR PHARMACEUTICAL PRODUCT

BACKGROUND OF THE INVENTION

The present invention concerns the field of cosmetology and pharmacology, in particular cutaneous and capillary applications, and relates to the use of at least one *Irvingia gabonensis* extract in a cosmetic and/or pharmaceutical product for the skin and/or the superficial body growths and to a cosmetic and/or pharmaceutical product containing such extract(s).

DESCRIPTION OF THE RELATED ART

*Irvingia gabonensis* (also known as the wild mango tree) is a tree which is prevalent in the rain forests of Central and West Africa and of which the oblong fruit has a hard stone surrounded by fibrous, edible flesh and containing two seeds resembling almonds.

These seeds, which are crushed and mixed with water, pepper or other condiments, are widely used in Africa as a thickener in the preparation of soups.

The chemical composition of the Irvingia seed is as follows, according to the literature (see OL OKE, Nutrition reports international, 1978, vol. 17 No. 3, 293–297 and ONYECHI E. N., Food Chemistry, 1995, 53.2, 173–175):

| | |
|---|---|
| proteins: | 8.8–10.6% |
| lipids: | 55–62.2% |
| carbohydrates: | 19.2–19.6% |
| fibers: | 8.2% |

The oil of *Irvingia gabonensis* seeds, which is solid at ambient temperature, contains, in particular, 55 to 59% of myristic acid and 35 to 36.3% of lauric acid.

The potential use of Irvingia fat in the preparation of margarine, kitchen oil, soap and pharmaceutical products has been mentioned. This fat has been investigated, in particular, for the preparation of suppositories or as a lubricant for granules or tablets.

Furthermore, the use of *Irvingia gabonensis* polysaccharides as thickeners or as sources of carbohydrates for diabetics in food products and as thickeners or binders in the pharmaceutical industry has been mentioned.

SUMMARY OF THE INVENTION

Now the inventors of the present invention have unexpectedly and surprisingly found that, apart from their known thickening properties, the extracts of *Irvingia gabonensis*, in particular the polysaccharide fractions of *Irvingia gabonensis*, could be used directly in cosmetic and pharmaceutical products for external application and had immediate properties which were more varied and quantitatively greater than the polysaccharides already used at present in cosmetic or pharmaceutical products, namely moisturising, film-forming, softening and restructuring properties.

Similarly, it has been found that the lipidic or fatty fraction could also be used in such products and had particular properties such as good chemical stability and weak colouring.

Thus, the general object of the present invention is to use at least one *Irvingia gabonensis* extract as active agent(s) for the preparation of a cosmetic and/or pharmaceutical product for topical use for the skin and/or the superficial body growths, this or these extract(s) preferably being obtained from the seeds of the *Irvingia gabonensis* tree.

DESCRIPTION OF THE PREFERRED EMBODIMENTS

According to a first embodiment of the invention, the extract used consists of the polysaccharide fraction of the seeds, optionally in the form of crude polysaccharide extract.

According to a second preferred embodiment of the invention, the extract used consists of a part of the polysaccharide fraction of the seeds, optionally in the form of a purified polysaccharide.

In this case, the polysaccharide fraction or the polysaccharide is preferably extracted from the seeds of the *Irvingia gabonensis* tree by water or aqueous solutions with a neutral, alkaline or acidic pH.

Finally, according to a third embodiment of the invention, the extract used can consist of the lipidic or fatty fraction of *Irvingia gabonensis* seeds alone or associated with the polysaccharide fraction or a part of the polysaccharide fraction of said seeds.

The processes for obtaining and preparing the various extracts of *Irvingia gabonensis* mentioned above lie within the general knowledge of a person skilled in the art in the field of cosmetology and pharmacology.

Various possible processes for obtaining extracts from *Irvingia gabonensis* seeds, in particular fat and polysaccharides, used in the context of the present invention will be described hereinafter as non-limiting embodiments.

EXAMPLE 1

950 grams of *Irvingia gabonensis* seeds are firstly crushed then extracted for one hour at ambient temperature in 3 liters of hexane.

After decantation for one night at ambient temperature, the hexane phase is removed, filtered and concentrated in a rotating evaporator.

After oven drying, 415.6 grams of a pale yellow solid oil are obtained.

One liter of solvent is then added to the reactor and extraction is repeated for 2 hours at 45° C. All the extract is filtered and the filtrate treated as hereinbefore: 182.7 grams of oil are thus obtained.

The residue is extracted again in 2.50 liter of hexane for 2 hours at 45° C. and is treated as before: 84.4 grams of oil are finally obtained.

The total crude oil yield of this process is 71.8%.

The crude *Irvingia gabonensis* oil can be refined and deodorised by conventional techniques known to a person skilled in the art to yield a white, perfectly odourless solid oil.

The residue which is insoluble in hexane is a beige powder representing 260 grams, that is 27% by weight relative to the total initial seed.

EXAMPLE 2

100 grams of residues which are insoluble in hexane and are obtained by the process described in example 1 are homogenised in 1.5 liters of distilled water.

Extraction is then carried out for 3 hours at 70° C.

After cooling, the viscous suspension is centrifuged for 15 minutes at 5,000 g.

The supernatant liquid is filtered over a nylon cloth in order to retain a slight lipidic layer.

790 ml of beige viscous supernatant liquid containing 3.9% of dry extract are thus collected and constitute the crude polysaccharides.

These polysaccharides are precipitated in fibre form by addition with stirring into two volumes of absolute ethanol.

These fibres are recovered by filtration, spin dried, washed in ethanol, then in acetone and finally dried in air then in an oven at 40° C.

15.1 grams of polysaccharides are thus obtained, that is a yield of 4.1% by weight relative to the total original seed.

EXAMPLE 3

100 grams of seeds are crushed then extracted in 2 liters of water for 2 hours at 50° C.

The solution is cooled to 30° C. then centrifuged for 15 minutes to 5,000 g.

The upper phase (layer of fat) is eliminated, the aqueous phase is filtered over cloth and 1.55 liters of supernatant are collected.

The supernatant is again centrifuged and the polysaccharides are then precipitated in two volumes of absolute ethanol then treated as in example 2.

4.2 grams of polysaccharides are thus obtained, that is a yield of 4.2% relative to the total original seed.

The extracts of *Irvingia gabonensis* seeds obtained, in particular, by any one of the above-described processes, in particular the polysaccharides, will be used in preparations for the care of the skin and superficial body growths as emollient, smoothing, repairing, moisturising and elasticising agents.

Said polysaccharides could be used in crude or purified form, in anhydrous form or in the form of aqueous solutions incorporated in a wide variety of cosmetic forms such as lotions, hydrogels, oil-in-water and water-in-oil emulsions, microemulsions, skin care products, hair care products, etc.

The present invention also relates to a cosmetic and/or pharmaceutical product for external use for the skin and/or the superficial body growths, characterised in that it contains between 0.05% and 50.00% by weight of one or more extracts of *Irvingia gabonensis* seeds.

According to a particular embodiment of the invention, said cosmetic and/or pharmaceutical product can advantageously consist of a treatment composition containing between 0.05% and 15.00% by weight of one or more extracts of *Irvingia gabonensis* seeds.

Various cosmetic or dermatological products or preparations containing one or more extracts of *Irvingia gabonensis* seeds will be described hereinafter as non-limiting examples of practical embodiments of the invention.

EXAMPLE 1

A cosmetic product according to the invention in the form of a hair rinsing emulsion could have a composition by weight, for example, made up of the following fractions A and B as mentioned hereinafter.

| Fraction A: | |
|---|---|
| glycerol stearate (and) Ceteareth 20 | 5.00% |
| lipidic Irvingia gabonensis extract | 1.00% |
| seeds (prepared by the process of example 1) | |
| Fraction B: | |
| dimethicone propyl PG betaine | 3.00% |
| trimonium Behen chloride | 1.00% |
| distilled water | 90.00% |
| fragrance | qsp |
| preservative | qsp |

The process for the preparation and manufacture of the aforementioned emulsion essentially involves, after mixing the components thereof, separately heating the fractions A and B to about 70° C., mixing and homogenising these two fractions and finally stirring the resultant mixture until it cools at ambient temperature.

EXAMPLE 2

A cosmetic product according to the invention in the form of a moisturising body lotion (oil-in-water) could have, for example, a composition by weight consisting of the following fractions A and B as indicated hereinafter:

| Fraction A: | |
|---|---|
| trilaureth phosphate-4 | 1.00% |
| polyglycerol stearate-2 PEG-4 | 4.00% |
| paraffin oil | 3.00% |
| cetostearyl isononanoate | 4.00% |
| lipidic Irvingia gabonensis extract | 4.00% |
| seeds (prepared by the process of example 1) | |
| isopropyl isostearate | 4.00% |
| antioxidant | qsp |
| Fraction B: | |
| carbomer | 0.30% |
| citric acid | 0.25% |
| glycerine | 3.00% |
| NaOH(N) | 1.50% |
| distilled water | 74.50% |
| preservative | qsp |
| polysaccharide Irvingia gabonensis extract | 3.00% |
| seeds (prepared by the process of example 2) | |
| fragrance | qsp |

The process for preparing and producing the aforementioned moisturising lotion essentially involves mixing the components of the fatty fraction A and heating them to 70° C., adding the Carbomer to them, mixing the other components of the aqueous fraction B and heating them to 70° C., pouring fraction B into Fraction A and stirring the mixture until it cools to ambient temperature and, finally, homogenising the resultant emulsion.

EXAMPLE 3

A cosmetic product according to the invention in the form of a moisturising emollient smoothing cream (oil-in-water) for the skin could have, for example, a composition by weight made up of the following fractions A, B and C as indicated hereinafter.

| Fraction A: | |
| --- | --- |
| glycerol stearate (and) Steareth-25 (and) Ceteth-20 (and) stearyl alcohol | 8.00% |
| stearyl alcohol | 1.00% |
| caprylic/capric acid triglyceride | 3.00% |
| stearoxylic dimethicone | 3.00% |
| lipidic Irvingia gabonensis extract seeds (prepared by the process in example 1) | 3.00% |
| Fraction B: | |
| glycerol | 3.00% |
| polysaccharide Irvingia gabonensis extract seeds (prepared by the process in example 2) | 2.00% |
| distilled water | 77.00% |
| Fraction C: | |
| fragrance | qsp |
| preservative | qsp |

The process for the preparation and production of the aforementioned cream essentially involves mixing and heating the fatty fraction A to 90° C., preparing the aqueous fraction B by stirring at 75° C., pouring the fraction A into the fraction B with turbine stirring, adding the fraction C, stopping turbine stirring at about 50° C. and carrying out planetary stirring until it cools at ambient temperature.

What is claimed is:

1. Cosmetic product for external use for the skin, comprising between 0.05% and 50.00% by weight of at least one extract of *Irvingia gabonensis* seeds.

2. Cosmetic product for external use for the skin and external body growths, comprising a treatment composition containing between 0.05% and 15.00% by weight of at least one extract of *Irvingia gabonensis* seeds.

3. Pharmaceutical product for external use for the skin, comprising between 0.05% and 50.00% by weight of at least one extract of *Irvingia gabonensis* seeds.

4. Pharmaceutical product for external use for the skin and superficial body growths, comprising a treatment composition containing between 0.05% and 15.00% by weight of at least one extract of *Irvingia gabonensis* seeds.

5. A method of preparing a topical-use product, comprising the step of including at least one *Irvingia gabonensis* extract as an active agent in the topical-use product.

6. The method of claim 5, wherein the product is a cosmetic for topical use on the skin and superficial body growths.

7. The method of claim 5, wherein the product is a pharmaceutical product for topical use on the skin and superficial body growths.

8. The method of claim 5, comprising the further step of obtaining the at least one *Irvingia gabonensis* extract from seeds of an *Irvingia gabonensis* tree.

9. The method of claim 8, wherein the *Irvingia gabonensis* extract consists of a polysaccharide fraction of the seeds of the *Irvingia gabonensis* tree.

10. The method of claim 8, wherein the polysaccharide fraction is in the form of a crude polysaccharide extract.

11. The method of claim 8, wherein the *Irvingia gabonensis* extract consists of a part of a polysaccharide fraction of the seeds of an *Irvingia gabonensis* tree.

12. The method of claims 8, wherein the part of the polysaccharide fraction is in the form of a purified polysaccharide.

13. The method of claim 11, comprising the further step of extracting the polysaccharide fraction from the seeds of the *Irvingia gabonensis* tree by water or aqueous solution.

14. The method of claim 12, comprising the further step of extracting the polysaccharide from the seeds of the *Irvingia gabonensis* tree by water or aqueous solution.

15. The method of claim 5, wherein the *Irvingia gabonensis* extract comprises a lipidic fraction obtained from *Irvingia gabonensis* seeds together with a least a part of a polysaccharide fraction of the *Irvingia gabonensis* seeds.

16. The method of claim 15, wherein the *Irvingia gabonensis* extracts consists of a lipidic fraction.

17. The method of claim 5, wherein the *Irvingia gabonensis* extract comprises a fatty fraction obtained from *Irvingia gabonensis* seeds together with a least a part of a polysaccharide fraction of the *Irvingia gabonensis* seeds.

18. The method of claim 17, wherein the *Irvingia gabonensis* extracts consists of a fatty fraction.

\* \* \* \* \*